(12) United States Patent
Denenburg et al.

(10) Patent No.: US 8,852,145 B2
(45) Date of Patent: Oct. 7, 2014

(54) INLINE LIQUID DRUG MEDICAL DEVICE HAVING ROTARY FLOW CONTROL MEMBER

(75) Inventors: Igor Denenburg, Gedera (IL); Nimrod Lev, Savion (IL); Moshe Gilboa, Kfar Saba (IL)

(73) Assignee: MEDIMOP Medical Projects, Ltd., Ra'anana (IL)

(*) Notice: Subject to any disclaimer, the term of this patent is extended or adjusted under 35 U.S.C. 154(b) by 0 days.

(21) Appl. No.: 13/884,981

(22) PCT Filed: Oct. 27, 2011

(86) PCT No.: PCT/IL2011/000829
§ 371 (c)(1),
(2), (4) Date: May 13, 2013

(87) PCT Pub. No.: WO2012/063230
PCT Pub. Date: May 18, 2012

(65) Prior Publication Data
US 2013/0237904 A1   Sep. 12, 2013

(30) Foreign Application Priority Data
Nov. 14, 2010 (IL) .......................................... 209290

(51) Int. Cl.
*A61M 37/00* (2006.01)
*A61M 5/32* (2006.01)
*A61J 1/20* (2006.01)

(52) U.S. Cl.
CPC ......... *A61M 5/3294* (2013.01); *A61J 2001/201* (2013.01); *A61J 1/2096* (2013.01)
USPC .............................................. 604/89; 604/87

(58) Field of Classification Search
CPC ..... A61J 1/20; A61J 1/2096; A61J 2001/201; A61J 2001/206; A61J 2001/2048; A61J 2001/2055; Y10S 604/905
USPC .......................................... 604/82–86, 87–91
See application file for complete search history.

(56) References Cited

U.S. PATENT DOCUMENTS

| | | | |
|---|---|---|---|
| 62,333 | A | 2/1867 | Holl |
| 1,021,681 | A | 3/1912 | Jennings |

(Continued)

FOREIGN PATENT DOCUMENTS

| | | |
|---|---|---|
| CN | 1950049 A | 4/2007 |
| DE | 1913926 A1 | 9/1970 |

(Continued)

OTHER PUBLICATIONS

Grifols Vial Adapter Product Literature, 2 pages, Jan. 2002.

(Continued)

*Primary Examiner* — Theodore Stigell
*Assistant Examiner* — Benjamin Koo
(74) *Attorney, Agent, or Firm* — Panitch Schwarze Belisario & Nadel LLP

(57) ABSTRACT

Inline liquid drug medical devices for use with a source of physiological fluid and a medicinal vessel for liquid drug reconstitution and administration purposes. The inline liquid drug medical devices include a housing having a longitudinal device axis, a rotary flow control member and a vial adapter for transposing the flow control member from an initial first flow control position for liquid drug reconstitution purposes to a second flow control position for liquid drug administration purposes. The inline liquid drug medical devices include a syringe port and a drug dispensing port co-axial with the device axis. The rotary flow control member is rotatable about an axis of rotation co-axial with the syringe port and the drug dispensing port.

4 Claims, 6 Drawing Sheets

(56) References Cited

U.S. PATENT DOCUMENTS

| | | |
|---|---|---|
| 1,704,817 A | 3/1929 | Ayers |
| 1,930,944 A | 10/1933 | Schmitz, Jr. |
| 2,326,490 A | 8/1943 | Perelson |
| 2,931,668 A | 4/1960 | Baley |
| 2,968,497 A | 1/1961 | Treleman |
| 3,059,643 A | 10/1962 | Barton |
| D198,499 S | 6/1964 | Harautuneian |
| 3,484,849 A | 12/1969 | Huebner et al. |
| 3,618,637 A | 11/1971 | Santomieri |
| 3,757,981 A | 9/1973 | Harris, Sr. et al. |
| 3,788,524 A | 1/1974 | Davis et al. |
| 3,822,700 A | 7/1974 | Pennington |
| 3,826,261 A | 7/1974 | Killinger |
| 3,872,992 A | 3/1975 | Larson |
| 3,885,607 A | 5/1975 | Peltier |
| 3,938,520 A | 2/1976 | Scislowicz et al. |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,051,852 A | 10/1977 | Villari |
| 4,109,670 A | 8/1978 | Slagel |
| 4,121,585 A | 10/1978 | Becker, Jr. |
| 4,161,178 A | 7/1979 | Genese |
| 4,187,848 A | 2/1980 | Taylor |
| 4,203,067 A | 5/1980 | Fitzky et al. |
| 4,203,443 A | 5/1980 | Genese |
| 4,210,173 A | 7/1980 | Choksi et al. |
| D257,286 S | 10/1980 | Folkman |
| 4,253,501 A | 3/1981 | Ogle |
| 4,296,786 A | 10/1981 | Brignola |
| 4,303,067 A | 12/1981 | Connolly et al. |
| 4,312,349 A | 1/1982 | Cohen |
| 4,314,586 A | 2/1982 | Folkman |
| 4,328,802 A | 5/1982 | Curley et al. |
| 4,335,717 A | 6/1982 | Bujan et al. |
| D267,199 S | 12/1982 | Koenig |
| 4,376,634 A | 3/1983 | Prior et al. |
| D268,871 S | 5/1983 | Benham et al. |
| 4,392,850 A | 7/1983 | Elias et al. |
| 4,410,321 A | 10/1983 | Pearson et al. |
| 4,411,662 A | 10/1983 | Pearson |
| D271,421 S | 11/1983 | Fetterman |
| 4,434,823 A | 3/1984 | Hudspith |
| 4,465,471 A | 8/1984 | Harris et al. |
| 4,475,915 A | 10/1984 | Sloane |
| 4,493,348 A | 1/1985 | Lemmons |
| 4,505,709 A | 3/1985 | Froning et al. |
| 4,507,113 A | 3/1985 | Dunlap |
| D280,018 S | 8/1985 | Scott |
| 4,532,969 A | 8/1985 | Kwaan |
| 4,564,054 A | 1/1986 | Gustavsson |
| 4,573,993 A | 3/1986 | Hoag et al. |
| 4,576,211 A | 3/1986 | Valentini et al. |
| 4,581,014 A | 4/1986 | Millerd et al. |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,676,530 A | 6/1987 | Nordgren et al. |
| 4,683,975 A | 8/1987 | Booth et al. |
| 4,697,622 A | 10/1987 | Swift et al. |
| 4,721,133 A | 1/1988 | Sundblom |
| 4,729,401 A | 3/1988 | Raines |
| 4,735,608 A | 4/1988 | Sardam |
| 4,743,229 A | 5/1988 | Chu |
| 4,743,243 A | 5/1988 | Vaillancourt |
| 4,752,292 A | 6/1988 | Lopez et al. |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,797,898 A | 1/1989 | Martinez |
| 4,804,366 A | 2/1989 | Zdeb et al. |
| 4,832,690 A | 5/1989 | Kuu |
| 4,834,152 A | 5/1989 | Howson et al. |
| 4,857,062 A | 8/1989 | Russell |
| 4,865,592 A | 9/1989 | Rycroft |
| 4,898,209 A | 2/1990 | Zbed |
| 4,909,290 A | 3/1990 | Coccia |
| 4,931,040 A | 6/1990 | Haber et al. |
| 4,932,944 A | 6/1990 | Jagger et al. |
| 4,967,797 A | 11/1990 | Manska |
| D314,050 S | 1/1991 | Sone |
| D314,622 S | 2/1991 | Andersson et al. |
| 4,997,430 A | 3/1991 | Van der Heiden et al. |
| 5,006,114 A | 4/1991 | Rogers et al. |
| 5,035,686 A | 7/1991 | Crittenden et al. |
| 5,041,105 A | 8/1991 | D'Alo et al. |
| 5,045,066 A | 9/1991 | Scheuble et al. |
| 5,049,129 A | 9/1991 | Zdeb et al. |
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,125,915 A | 6/1992 | Berry et al. |
| D328,788 S | 8/1992 | Sagae et al. |
| 5,171,230 A | 12/1992 | Eland et al. |
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |
| 5,232,029 A | 8/1993 | Knox et al. |
| 5,232,109 A | 8/1993 | Tirrell et al. |
| 5,242,432 A | 9/1993 | DeFrank |
| 5,247,972 A | 9/1993 | Tetreault |
| D341,420 S | 11/1993 | Conn |
| 5,269,768 A | 12/1993 | Cheung |
| 5,270,219 A | 12/1993 | DeCastro et al. |
| 5,279,576 A | 1/1994 | Loo et al. |
| 5,288,290 A | 2/1994 | Brody |
| 5,300,034 A | 4/1994 | Behnke et al. |
| 5,301,685 A | 4/1994 | Guirguis |
| 5,304,163 A | 4/1994 | Bonnici et al. |
| 5,308,483 A | 5/1994 | Sklar et al. |
| 5,312,377 A | 5/1994 | Dalton |
| 5,328,474 A | 7/1994 | Raines |
| D349,648 S | 8/1994 | Tirrell et al. |
| 5,334,163 A | 8/1994 | Sinnett |
| 5,334,179 A | 8/1994 | Poli et al. |
| 5,342,346 A | 8/1994 | Honda et al. |
| 5,344,417 A | 9/1994 | Wadsworth, Jr. |
| 5,350,372 A | 9/1994 | Ikeda et al. |
| 5,364,386 A | 11/1994 | Fukuoka et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,492,147 A | 2/1996 | Challender et al. |
| D369,406 S | 4/1996 | Niedospial et al. |

(56) References Cited

U.S. PATENT DOCUMENTS

| | | |
|---|---|---|
| 5,505,714 A | 4/1996 | Dassa et al. |
| 5,509,433 A | 4/1996 | Paradis |
| 5,520,659 A | 5/1996 | Hedges |
| 5,526,853 A | 6/1996 | McPhee et al. |
| 5,527,306 A | 6/1996 | Haining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley, III et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,674,195 A | 10/1997 | Truthan |
| 5,676,346 A | 10/1997 | Leinsing |
| 5,685,845 A | 11/1997 | Grimard |
| 5,699,821 A | 12/1997 | Paradis |
| 5,702,019 A | 12/1997 | Grimard |
| 5,718,346 A | 2/1998 | Weiler |
| D393,722 S | 4/1998 | Fangrow, Jr. et al. |
| 5,738,144 A | 4/1998 | Rogers |
| 5,743,312 A | 4/1998 | Pfeifer et al. |
| 5,746,733 A | 5/1998 | Capaccio et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Muller |
| 5,806,831 A | 9/1998 | Paradis |
| 5,810,792 A | 9/1998 | Fangrow, Jr. et al. |
| D399,559 S | 10/1998 | Molina |
| 5,817,082 A | 10/1998 | Niedospial, Jr. et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,839,715 A | 11/1998 | Leinsing |
| 5,853,406 A | 12/1998 | Masuda et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A | 4/1999 | Peterson et al. |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial, Jr. et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial, Jr. et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,944,700 A | 8/1999 | Nguyen et al. |
| 5,954,104 A | 9/1999 | Daubert et al. |
| 5,971,181 A | 10/1999 | Niedospial, Jr. et al. |
| 5,971,965 A | 10/1999 | Mayer |
| 5,989,237 A | 11/1999 | Fowles et al. |
| 6,003,566 A | 12/1999 | Thibault et al. |
| 6,004,278 A | 12/1999 | Botich et al. |
| 6,019,750 A | 2/2000 | Fowles et al. |
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote, Sr. et al. |
| D422,357 S | 4/2000 | Niedospial, Jr. et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| 6,086,762 A | 7/2000 | Guala |
| 6,089,541 A | 7/2000 | Weinheimer et al. |
| 6,090,091 A | 7/2000 | Fowles et al. |
| 6,090,093 A | 7/2000 | Thibault et al. |
| 6,099,511 A | 8/2000 | Devos et al. |
| 6,113,068 A | 9/2000 | Ryan |
| 6,113,583 A | 9/2000 | Fowles et al. |
| 6,117,114 A | 9/2000 | Paradis |
| 6,139,534 A | 10/2000 | Niedospial, Jr. et al. |
| 6,142,446 A | 11/2000 | Leinsing |
| 6,146,362 A | 11/2000 | Turnbull et al. |
| 6,149,623 A | 11/2000 | Reynolds |
| 6,156,025 A | 12/2000 | Niedospial, Jr. et al. |
| 6,159,192 A | 12/2000 | Fowles et al. |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |
| 6,174,304 B1 | 1/2001 | Weston |
| 6,179,822 B1 | 1/2001 | Niedospial, Jr. |
| 6,179,823 B1 | 1/2001 | Niedospial, Jr. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial, Jr. |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |
| 6,296,621 B1 | 10/2001 | Masuda et al. |
| 6,299,131 B1 | 10/2001 | Ryan |
| 6,343,629 B1 | 2/2002 | Wessman et al. |
| 6,348,044 B1 | 2/2002 | Coletti et al. |
| 6,358,236 B1 | 3/2002 | DeFoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| 6,382,442 B1 | 5/2002 | Thibault et al. |
| 6,408,897 B1 | 6/2002 | Laurent et al. |
| 6,409,708 B1 | 6/2002 | Wessman |
| 6,440,107 B1 | 8/2002 | Trombley, III et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial, Jr. et al. |
| 6,503,240 B1 | 1/2003 | Niedospial, Jr. et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |

(56) References Cited

U.S. PATENT DOCUMENTS

| | | |
|---|---|---|
| D472,630 S | 4/2003 | Douglas et al. |
| 6,544,246 B1 | 4/2003 | Niedospial, Jr. |
| 6,551,299 B2 | 4/2003 | Miyoshi et al. |
| 6,558,365 B2 | 5/2003 | Zinger et al. |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,582,415 B1 | 6/2003 | Fowles et al. |
| 6,591,876 B2 | 7/2003 | Safabash |
| 6,601,721 B2 | 8/2003 | Jansen et al. |
| 6,626,309 B1 | 9/2003 | Jansen et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial, Jr. |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,695,829 B2 | 2/2004 | Hellstrom et al. |
| 6,699,229 B2 | 3/2004 | Zinger et al. |
| 6,706,022 B1 | 3/2004 | Leinsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Arnissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Leinsing et al. |
| 6,832,994 B2 | 12/2004 | Niedospial, Jr. et al. |
| 6,852,103 B2 * | 2/2005 | Fowles et al. ............... 604/413 |
| 6,875,203 B1 | 4/2005 | Fowles et al. |
| 6,875,205 B2 | 4/2005 | Leinsing |
| 6,878,131 B2 | 4/2005 | Novacek et al. |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,957,745 B2 | 10/2005 | Thibault et al. |
| RE38,996 E | 2/2006 | Crawford et al. |
| 6,994,315 B2 | 2/2006 | Ryan et al. |
| 6,997,916 B2 | 2/2006 | Simas, Jr. et al. |
| 6,997,917 B2 | 2/2006 | Niedospial, Jr. et al. |
| 7,024,968 B2 | 4/2006 | Raudabough et al. |
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |
| 7,100,890 B2 | 9/2006 | Cote, Sr. et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| 7,241,285 B1 | 7/2007 | Dikeman |
| 7,294,122 B2 | 11/2007 | Kubo et al. |
| 7,306,199 B2 | 12/2007 | Leinsing et al. |
| D561,348 S | 2/2008 | Zinger et al. |
| 7,326,188 B1 | 2/2008 | Russell et al. |
| 7,326,194 B2 | 2/2008 | Zinger et al. |
| 7,350,764 B2 | 4/2008 | Raybuck |
| 7,354,422 B2 | 4/2008 | Riesenberger et al. |
| 7,354,427 B2 | 4/2008 | Fangrow |
| 7,425,209 B2 | 9/2008 | Fowles et al. |
| 7,435,246 B2 | 10/2008 | Zihlmann |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| 7,654,995 B2 | 2/2010 | Warren et al. |
| 7,670,326 B2 | 3/2010 | Shemesh |
| 7,695,445 B2 | 4/2010 | Yuki |
| D616,090 S | 5/2010 | Kawamura |
| 7,713,247 B2 | 5/2010 | Lopez |
| 7,717,886 B2 | 5/2010 | Lopez |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosler et al. |
| 7,744,581 B2 | 6/2010 | Wallen et al. |
| 7,758,082 B2 | 7/2010 | Weigel et al. |
| 7,762,524 B2 | 7/2010 | Cawthon et al. |
| 7,766,304 B2 | 8/2010 | Phillips |
| 7,771,383 B2 | 8/2010 | Truitt et al. |
| 7,799,009 B2 | 9/2010 | Niedospial, Jr. et al. |
| 7,803,140 B2 | 9/2010 | Fangrow, Jr. |
| D627,216 S | 11/2010 | Fulginiti |
| D630,732 S | 1/2011 | Lev et al. |
| 7,862,537 B2 | 1/2011 | Zinger et al. |
| 7,867,215 B2 | 1/2011 | Akerlund et al. |
| 7,879,018 B2 | 2/2011 | Zinger et al. |
| D634,007 S | 3/2011 | Zinger et al. |
| 7,900,659 B2 | 3/2011 | Whitley et al. |
| D637,713 S | 5/2011 | Nord et al. |
| 7,985,216 B2 | 7/2011 | Daily et al. |
| D644,104 S | 8/2011 | Maeda et al. |
| 7,993,328 B2 | 8/2011 | Whitley |
| 8,012,132 B2 | 9/2011 | Lum et al. |
| 8,016,809 B2 | 9/2011 | Zinger et al. |
| 8,021,325 B2 | 9/2011 | Zinger et al. |
| 8,025,653 B2 | 9/2011 | Capitaine et al. |
| 8,029,472 B2 | 10/2011 | Leinsing et al. |
| 8,038,123 B2 | 10/2011 | Ruschke et al. |
| 8,066,688 B2 | 11/2011 | Zinger et al. |
| 8,070,739 B2 | 12/2011 | Zinger et al. |
| 8,075,550 B2 | 12/2011 | Nord et al. |
| 8,096,525 B2 | 1/2012 | Ryan |
| 8,105,314 B2 | 1/2012 | Fangrow, Jr. |
| D655,017 S | 2/2012 | Mosler et al. |
| 8,122,923 B2 | 2/2012 | Kraus et al. |
| 8,123,736 B2 | 2/2012 | Kraushaar et al. |
| D655,071 S | 3/2012 | Davila |
| 8,157,784 B2 | 4/2012 | Rogers |
| 8,167,863 B2 | 5/2012 | Yow |
| 8,172,824 B2 | 5/2012 | Pfeifer et al. |
| 8,177,768 B2 | 5/2012 | Leinsing |
| 8,182,452 B2 | 5/2012 | Mansour et al. |
| 8,187,248 B2 | 5/2012 | Zihlmann |
| 8,196,614 B2 | 6/2012 | Kriheli |
| 8,197,459 B2 | 6/2012 | Jansen et al. |
| 8,211,069 B2 | 7/2012 | Fangrow, Jr. |
| 8,225,959 B2 | 7/2012 | Lambrecht |
| 8,241,268 B2 | 8/2012 | Whitley |
| 8,262,628 B2 | 9/2012 | Fangrow, Jr. |
| 8,262,641 B2 | 9/2012 | Vedrine et al. |

(56) References Cited

U.S. PATENT DOCUMENTS

| | | |
|---|---|---|
| 8,267,127 B2 | 9/2012 | Kriheli |
| D669,980 S | 10/2012 | Lev et al. |
| 8,287,513 B2 | 10/2012 | Ellstrom et al. |
| D673,673 S | 1/2013 | Wang |
| D674,088 S | 1/2013 | Lev et al. |
| D681,230 S | 4/2013 | Mosler et al. |
| 8,454,573 B2 | 6/2013 | Wyatt et al. |
| 8,469,939 B2 | 6/2013 | Fangrow, Jr. |
| 8,475,404 B2 | 7/2013 | Foshee et al. |
| 8,480,645 B1 | 7/2013 | Choudhury et al. |
| 8,480,646 B2 | 7/2013 | Nord et al. |
| 8,506,548 B2 | 8/2013 | Okiyama |
| 8,511,352 B2 | 8/2013 | Kraus et al. |
| D690,418 S | 9/2013 | Rosenquist |
| 8,523,837 B2 | 9/2013 | Wiggins et al. |
| 8,545,476 B2 | 10/2013 | Ariagno et al. |
| 8,551,067 B2 | 10/2013 | Zinger et al. |
| 8,556,879 B2 | 10/2013 | Okiyama |
| 8,562,582 B2 | 10/2013 | Tuckwell et al. |
| 8,608,723 B2 | 12/2013 | Lev et al. |
| 8,628,508 B2 | 1/2014 | Weitzel et al. |
| 8,684,992 B2 | 4/2014 | Sullivan et al. |
| 2001/0000347 A1 | 4/2001 | Hellstrom et al. |
| 2001/0025671 A1 | 10/2001 | Safabash |
| 2001/0029360 A1 | 10/2001 | Miyoshi et al. |
| 2001/0051793 A1 | 12/2001 | Weston |
| 2002/0017328 A1 | 2/2002 | Loo |
| 2002/0066715 A1 | 6/2002 | Niedospial |
| 2002/0087118 A1 | 7/2002 | Reynolds et al. |
| 2002/0087141 A1 | 7/2002 | Zinger et al. |
| 2002/0087144 A1 | 7/2002 | Zinger et al. |
| 2002/0121496 A1 | 9/2002 | Thiebault et al. |
| 2002/0123736 A1 | 9/2002 | Fowles et al. |
| 2002/0127150 A1 | 9/2002 | Sasso |
| 2002/0128628 A1 | 9/2002 | Fathallah |
| 2002/0138045 A1 | 9/2002 | Moen |
| 2002/0173752 A1 | 11/2002 | Polzin |
| 2002/0193777 A1 | 12/2002 | Aneas |
| 2003/0028156 A1 | 2/2003 | Juliar |
| 2003/0036725 A1 | 2/2003 | Lavi et al. |
| 2003/0068354 A1 | 4/2003 | Reif et al. |
| 2003/0073971 A1 | 4/2003 | Saker |
| 2003/0100866 A1 | 5/2003 | Reynolds |
| 2003/0109846 A1 | 6/2003 | Zinger et al. |
| 2003/0120209 A1 | 6/2003 | Jensen et al. |
| 2003/0153895 A1 | 8/2003 | Leinsing |
| 2003/0187420 A1 | 10/2003 | Akerlund et al. |
| 2003/0191445 A1 | 10/2003 | Wallen et al. |
| 2003/0195479 A1 | 10/2003 | Kuracina et al. |
| 2003/0199846 A1 | 10/2003 | Fowles et al. |
| 2003/0199847 A1 | 10/2003 | Akerlund et al. |
| 2004/0024354 A1 | 2/2004 | Reynolds |
| 2004/0039365 A1 | 2/2004 | Aramata et al. |
| 2004/0044327 A1 | 3/2004 | Hasegawa |
| 2004/0073189 A1 | 4/2004 | Wyatt et al. |
| 2004/0153047 A1 | 8/2004 | Blank et al. |
| 2004/0181192 A1 | 9/2004 | Cuppy |
| 2004/0204699 A1 | 10/2004 | Hanly et al. |
| 2004/0217315 A1 | 11/2004 | Doyle |
| 2004/0225274 A1 | 11/2004 | Jansen et al. |
| 2004/0236305 A1 | 11/2004 | Jansen et al. |
| 2004/0255952 A1 | 12/2004 | Carlsen et al. |
| 2005/0015070 A1 | 1/2005 | Delnevo et al. |
| 2005/0016626 A1 | 1/2005 | Wilcox et al. |
| 2005/0055008 A1 | 3/2005 | Paradis et al. |
| 2005/0082828 A1 | 4/2005 | Wicks et al. |
| 2005/0124964 A1 | 6/2005 | Niedospial et al. |
| 2005/0137566 A1 | 6/2005 | Fowles et al. |
| 2005/0148994 A1 | 7/2005 | Leinsing |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0079834 A1 | 4/2006 | Tennican et al. |
| 2006/0089594 A1 | 4/2006 | Landau |
| 2006/0089603 A1 | 4/2006 | Truitt et al. |
| 2006/0095015 A1 | 5/2006 | Hobbs et al. |
| 2006/0106360 A1 | 5/2006 | Wong |
| 2006/0135948 A1 | 6/2006 | Varma |
| 2006/0253084 A1 | 11/2006 | Nordgren |
| 2007/0024995 A1 | 2/2007 | Hayashi |
| 2007/0060904 A1 | 3/2007 | Vedrine et al. |
| 2007/0079894 A1 | 4/2007 | Kraus et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0106244 A1 | 5/2007 | Mosler et al. |
| 2007/0112324 A1 | 5/2007 | Hamedi-Sangsari |
| 2007/0156112 A1 | 7/2007 | Walsh |
| 2007/0167904 A1 | 7/2007 | Zinger et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0249995 A1 | 10/2007 | Van Manen |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2007/0299404 A1 | 12/2007 | Katoh et al. |
| 2008/0009789 A1* | 1/2008 | Zinger et al. .................. 604/89 |
| 2008/0009822 A1 | 1/2008 | Enerson |
| 2008/0172024 A1 | 7/2008 | Yow |
| 2008/0249479 A1 | 10/2008 | Zinger et al. |
| 2008/0249498 A1 | 10/2008 | Fangrow |
| 2008/0287905 A1 | 11/2008 | Hiejima et al. |
| 2008/0294100 A1 | 11/2008 | de Costa et al. |
| 2008/0306439 A1 | 12/2008 | Nelson et al. |
| 2008/0312634 A1 | 12/2008 | Helmerson et al. |
| 2009/0012492 A1 | 1/2009 | Zihlmann |
| 2009/0082750 A1 | 3/2009 | Denenburg et al. |
| 2009/0143758 A1 | 6/2009 | Okiyama |
| 2009/0177177 A1 | 7/2009 | Zinger et al. |
| 2009/0177178 A1 | 7/2009 | Pedersen |
| 2009/0187140 A1 | 7/2009 | Racz |
| 2009/0216212 A1 | 8/2009 | Fangrow, Jr. |
| 2009/0267011 A1 | 10/2009 | Hatton et al. |
| 2009/0299325 A1 | 12/2009 | Vedrine et al. |
| 2009/0326506 A1 | 12/2009 | Hasegawa et al. |
| 2010/0010443 A1 | 1/2010 | Morgan et al. |
| 2010/0022985 A1 | 1/2010 | Sullivan et al. |
| 2010/0030181 A1 | 2/2010 | Helle et al. |
| 2010/0036319 A1 | 2/2010 | Drake et al. |
| 2010/0076397 A1 | 3/2010 | Reed et al. |
| 2010/0087786 A1 | 4/2010 | Zinger et al. |
| 2010/0137827 A1 | 6/2010 | Warren et al. |
| 2010/0160889 A1 | 6/2010 | Smith et al. |
| 2010/0168712 A1 | 7/2010 | Tuckwell et al. |
| 2010/0179506 A1 | 7/2010 | Shemesh et al. |
| 2010/0204670 A1 | 8/2010 | Kraushaar et al. |
| 2010/0241088 A1 | 9/2010 | Ranalletta et al. |
| 2010/0274184 A1 | 10/2010 | Chun |
| 2010/0286661 A1 | 11/2010 | Raday et al. |
| 2010/0312220 A1 | 12/2010 | Kalitzki |
| 2011/0054440 A1 | 3/2011 | Lewis |
| 2011/0087164 A1 | 4/2011 | Mosler et al. |
| 2011/0160701 A1 | 6/2011 | Wyatt et al. |
| 2011/0224640 A1 | 9/2011 | Kuhn et al. |
| 2011/0230856 A1 | 9/2011 | Kyle et al. |
| 2011/0264037 A1 | 10/2011 | Foshee et al. |
| 2011/0264069 A1 | 10/2011 | Bochenko |
| 2011/0276007 A1 | 11/2011 | Denenburg |
| 2011/0319827 A1 | 12/2011 | Leinsing et al. |
| 2012/0022469 A1 | 1/2012 | Alpert |
| 2012/0053555 A1 | 3/2012 | Ariagno et al. |
| 2012/0059346 A1 | 3/2012 | Sheppard et al. |

(56) References Cited

U.S. PATENT DOCUMENTS

| | | |
|---|---|---|
| 2012/0067429 A1 | 3/2012 | Mosler et al. |
| 2012/0078214 A1 | 3/2012 | Finke et al. |
| 2012/0123382 A1 | 5/2012 | Kubo |
| 2012/0184938 A1 | 7/2012 | Lev et al. |
| 2012/0215182 A1 | 8/2012 | Mansour et al. |
| 2012/0220977 A1 | 8/2012 | Yow |
| 2012/0220978 A1 | 8/2012 | Lev et al. |
| 2012/0265163 A1 | 10/2012 | Cheng et al. |
| 2012/0296307 A1 | 11/2012 | Holt et al. |
| 2012/0310203 A1 | 12/2012 | Khaled et al. |
| 2012/0323187 A1 | 12/2012 | Iwase et al. |
| 2012/0323210 A1 | 12/2012 | Lev et al. |
| 2013/0053814 A1 | 2/2013 | Mueller-Beckhaus et al. |
| 2013/0096493 A1 | 4/2013 | Kubo et al. |
| 2013/0199669 A1 | 8/2013 | Moy et al. |
| 2013/0231630 A1 | 9/2013 | Kraus et al. |
| 2013/0237904 A1 | 9/2013 | Deneburg et al. |
| 2013/0289530 A1 | 10/2013 | Wyatt et al. |
| 2014/0150911 A1 | 6/2014 | Hanner et al. |

FOREIGN PATENT DOCUMENTS

| | | |
|---|---|---|
| DE | 4122476 A1 | 1/1993 |
| DE | 19504413 A1 | 8/1996 |
| DE | 202004012714 U1 | 11/2004 |
| DE | 202009011019 U1 | 12/2010 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0518397 A1 | 12/1992 |
| EP | 0521460 A1 | 1/1993 |
| EP | 0637443 A1 | 2/1995 |
| EP | 0737467 A1 | 10/1996 |
| EP | 761562 A1 | 3/1997 |
| EP | 765652 A1 | 4/1997 |
| EP | 765853 A1 | 4/1997 |
| EP | 0806597 A1 | 11/1997 |
| EP | 0814866 A1 | 1/1998 |
| EP | 829248 A2 | 3/1998 |
| EP | 0856331 A2 | 8/1998 |
| EP | 882441 A2 | 12/1998 |
| EP | 0887085 A2 | 12/1998 |
| EP | 0887885 A2 | 12/1998 |
| EP | 897708 A2 | 2/1999 |
| EP | 0898951 A2 | 3/1999 |
| EP | 960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| FR | 2029242 A5 | 10/1970 |
| FR | 2856660 A1 | 12/2004 |
| FR | 2869795 A1 | 11/2005 |
| FR | 2931363 A1 | 11/2009 |
| GB | 1444210 A | 7/1976 |
| IL | 171662 | 10/2005 |
| JP | 03-062426 B | 9/1991 |
| JP | 4329954 A | 11/1992 |
| JP | 06-050656 U | 7/1994 |
| JP | H08-000710 A | 1/1996 |
| JP | 09-104460 A | 4/1997 |
| JP | 09-104461 A | 4/1997 |
| JP | 10-118158 A | 5/1998 |
| JP | H10-504736 A | 5/1998 |
| JP | 11503627 T | 3/1999 |
| JP | 11-319031 A | 11/1999 |
| JP | 2000-508934 A | 7/2000 |
| JP | 2000-237278 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2004-097253 A | 4/2004 |
| JP | 2004-522541 A | 7/2004 |
| JP | 2010-179128 A | 8/2010 |
| WO | 9003536 A1 | 4/1990 |
| WO | 9403373 A1 | 2/1994 |
| WO | 9507066 A1 | 3/1995 |
| WO | 9600053 A1 | 1/1996 |
| WO | 9629113 A1 | 9/1996 |
| WO | 9736636 A1 | 10/1997 |
| WO | 9832411 A1 | 7/1998 |
| WO | 9837854 A1 | 9/1998 |
| WO | 9961093 A1 | 12/1999 |
| WO | 0128490 A1 | 4/2001 |
| WO | 0130425 A1 | 5/2001 |
| WO | 0132524 A1 | 5/2001 |
| WO | 0160311 A1 | 8/2001 |
| WO | 0191693 A2 | 12/2001 |
| WO | 0209797 A1 | 2/2002 |
| WO | 0232372 A1 | 4/2002 |
| WO | 0236191 A2 | 5/2002 |
| WO | 02066100 A2 | 8/2002 |
| WO | 02089900 A1 | 11/2002 |
| WO | 03051423 A2 | 6/2003 |
| WO | 03070147 A2 | 8/2003 |
| WO | 03079956 A1 | 10/2003 |
| WO | 2004041148 A1 | 5/2004 |
| WO | 2005002492 A1 | 1/2005 |
| WO | 2005041846 A2 | 5/2005 |
| WO | 2005105014 A2 | 11/2005 |
| WO | 2006099441 A1 | 9/2006 |
| WO | 2007015233 A1 | 2/2007 |
| WO | 2007017868 A1 | 2/2007 |
| WO | 2007052252 A1 | 5/2007 |
| WO | 2007101772 A1 | 9/2007 |
| WO | 2007105221 A1 | 9/2007 |
| WO | 2008126090 A1 | 10/2008 |
| WO | 2009026443 A2 | 2/2009 |
| WO | 2009029010 A1 | 3/2009 |
| WO | 2009038860 A1 | 3/2009 |
| WO | 2009038860 A2 | 3/2009 |
| WO | 2009040804 A2 | 4/2009 |
| WO | 2009087572 A1 | 7/2009 |
| WO | 2009093249 A1 | 7/2009 |
| WO | 2009112489 A1 | 9/2009 |
| WO | 2009146088 A1 | 12/2009 |
| WO | 2010061743 A1 | 6/2010 |
| WO | 2010117580 A1 | 10/2010 |
| WO | 2011039747 A1 | 4/2011 |
| WO | 2011058545 A1 | 5/2011 |
| WO | 2011058548 A1 | 5/2011 |
| WO | 2011077434 A1 | 6/2011 |
| WO | 2011104711 A1 | 9/2011 |
| WO | 2012063230 A1 | 5/2012 |
| WO | 2012143921 A1 | 10/2012 |
| WO | 2013127813 A1 | 9/2013 |
| WO | 2013134246 A1 | 9/2013 |
| WO | 2013156944 A1 | 10/2013 |
| WO | 2014033710 A1 | 3/2014 |

OTHER PUBLICATIONS

Novel Transfer, Mixing and Drug Delivery Systems, MOP Medimop Medical Projects Ltd. Catalog, 4 pages, Rev. 4, 2004.
Office Action Issued Oct. 6, 2003 in U.S. Appl. No. 10/062,796.
Office Action Issued Feb. 22, 2005 in U.S. Appl. No. 10/062,796.

(56) References Cited

OTHER PUBLICATIONS

Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/en/products/Pages/Mixject.aspx (admitted prior art).
http://www.westpharma.com/SiteCollectionDocuments/Recon/mixject%20product%20sheet.pdf; MIXJECT product information sheet pp. 1. (admitted prior art).
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376.
Int'l Search Report Issued Aug. 25, 2008 in Int'l Application No. PCT/IL2008/000517.
Written Opinion of the ISR Issued Oct. 17, 2009 in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued Jan. 20, 2010 in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
Int'l Search Report issued Oct. 7, 2011 in Int'l Application No. PCT/IL2011/000511.
Int'l Search Report issued Mar. 6, 2012 in Int'l Application No. PCT/IL2011/000834; Written Opinion.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 2008801108283.4.
Office Action issued Mar. 6, 2012 in U.S. Appl. No. 12/678,928.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
Alaris Medical Systems Product Brochure, 4 pages, Issue 1, Oct. 11, 1999.
Smart Site Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Int'l Search Report issued Aug. 16, 2012 in Int'l Application No. PCT/IL2012/000164.
U.S. Appl. No. 29/438,134 by Lev, filed Nov. 27, 2012.
U.S. Appl. No. 29/438,141 by Gilboa, filed Nov. 27, 2012.
Int'l Search Report issued Jan. 22, 2013 in Int'l Application No. PCT/IL2012/000354.
Int'l Search Report issued Mar. 18, 2013 in Int'l Application No. PCT/IL2012/050516.
Office Action issued Apr. 2, 2013 in U.S. Appl. No. 13/505,790.
Int'l Search Report and Written Opinion issued Mar. 6, 2012 in Int'l Application No. PCT/IL2011/000834.
U.S. Appl. No. 13/883,289 by Lev, filed May 3, 2013.
Office Action issued May 31, 2013 in U.S. Appl. No. 13/505,790.
Int'l Search Report issued Jun. 5, 2013 in Int'l Application No. PCT/IL2012/050407.
Int'l Search Report issued Jun. 19, 2013 in Int'l Application No. PCT/IL201/050167.
Int'l Search Report issued Jul. 1, 2013 in Int'l Application No. PCT/IL2013/050180.
Int'l Search Report issued Jul. 31, 2103 in Int'l Application No. PCT/IL2013/050313.
Int'l Search Report issued Jul. 26, 2013 in Int'l Application No. PCT/IL2013/050316.
English translation of an Office Action issued Jun. 19, 2013 in JP Application No. 2012-531551.
Office Action issued Aug. 20, 2013 in U.S. Appl. No. 13/576,461 by Lev.
International Search Report Issued Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).

(56) References Cited

OTHER PUBLICATIONS

Drug Adminsitration Systems product information sheets; http://www.westpharma.com/eu/en/products/Pages/Vial2Bag.aspx; pp. 1-3 (admitted prior art).
Office Action Issued Jun. 8, 2010 in U.S. Appl. No. 12/112,490 by Zinger.
Office Action issued Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
Office Action issued Jun. 15, 2011 in JP Application No. 2008-538492.
Translation of Office Action issued Jun. 18, 2012 in JP Application No. 2008-538492.
Translation of Office Action issued Apr. 15, 2013 in JP Application No. 2008-538492.
Office Action issued Jul. 13, 2012 in U.S. Appl. No. 12/112,490 by Zinger.
Office Action issued Jan. 23, 2013 in U.S. Appl. No. 12/112,490 by Zinger.
Int'l Preliminary Report on Patentability issued May 6, 2008 in Int'l Application No. PCT/IL2006/001228.
Written Opinion issued Aug. 16, 2012 in Int'l Application No. PCT/IL2012/000164.
English translation of an Office Action issued Sep. 10, 2013 in JP Application No. 2012-554468.
Office Action issued Nov. 11, 2013 in IL Application No. 218730.
U.S. Appl. No. 29/478,723 by Lev, filed Jan. 8, 2014.
U.S. Appl. No. 29/478,726 by Lev, filed Jan. 8, 2014.
Office Action issued Jan. 2, 2014 in U.S. Appl. No. 13/505,881 by Lev.
Int'l Search Report issued Jun. 19, 2013 in Int'l Application No. PCT/IL2013/050167.
Int'l Preliminary Report on Patentability issued Aug. 28, 2012 in Int'l Application No. PCT/IL2011/000186.
U.S. Appl. No. 14/005,751 by Denenburg, filed Sep. 17, 2013.
English translation of an Office Action issued Jul. 26, 2013 in JP Application No. 2012-538464.
Int'l Search Report & Written Opinion issued on Mar. 7, 2012 in Int'l Application No. PCT/IL2011/000829.
Int'l Search Report and Written Opinion issued Jan. 7, 2014 in Int'l Application No. PCT/IL2012/050721.
English translation of an Office Action issued Jan. 9, 2014 in JP Application No. 2010-526421.
English translation of an Office Action issued Dec. 4, 2013 in CN Application No. 201080051210.3.
English translation of an Office Action issued Dec. 25, 2013 in CN Application No. 201180006530.1.
Office Action issued Nov. 28, 2013 in IN Application No. 4348/DELNP/2008.
Office Action issued Oct. 8, 2013 in CN Application No. 201080043825.1.
Int'l Preliminary Report on Patentability issued Sep. 24, 2013 in Int'l Application No. PCT/IL2012/000354.
U.S. Appl. No. 14/345,094 by Lev, filed Mar. 14, 2014.
U.S. Appl. No. 14/366,306 by LEV, filed Jun. 18, 2014.
Office Action issued Apr. 17, 2014 in CN Application No. 201080051201.4.
Int'l Search Report and Written Opinion issued May 8, 2014 in Int'l Application No. PCT/IL2013/050706.
English translation of an Office Action issued Apr. 28, 2014 in JP Application No. 2013-537257.
Office Action issued May 6, 2014 in U.S. Appl. No. 13/505,881 by LEV.
Int'l Search Report and Written Opinion issued Jul. 16, 2014 in Int'l Application No. PCT/IL2014/050327.
English translation of an Office Action issued Jun. 30, 2014 in CN Application No. 201180052962.6.
Extended European Search Report issued Jun. 3, 2014 in EP Application No. 08781828.2.

\* cited by examiner

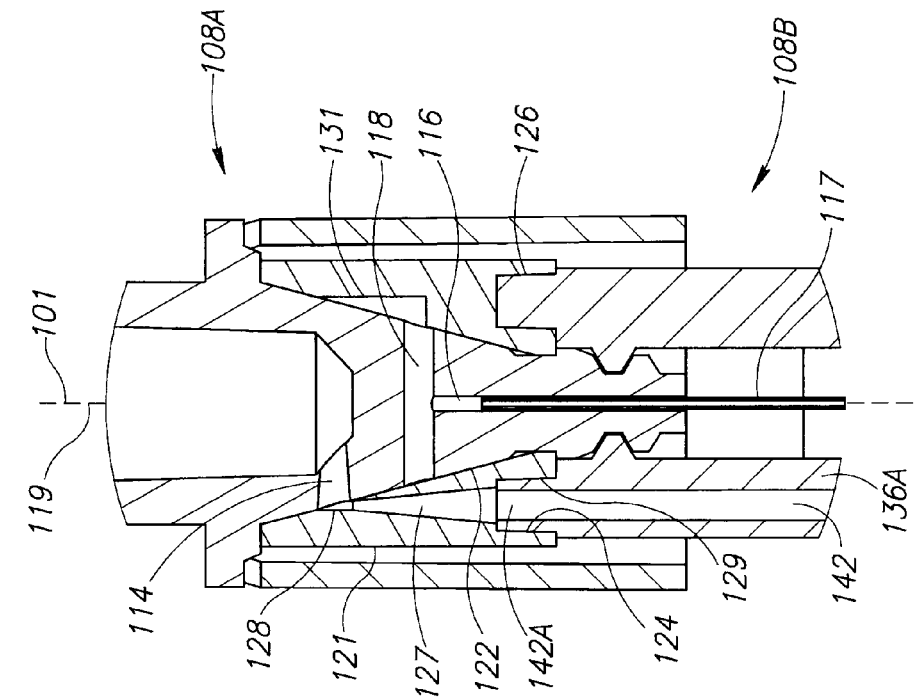
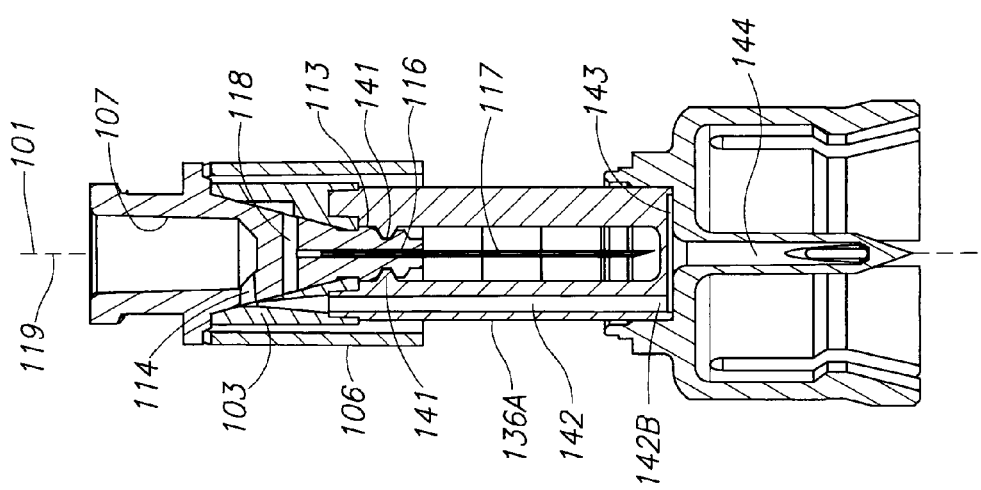
FIG. 4A
FIG. 4B

INLINE LIQUID DRUG MEDICAL DEVICE HAVING ROTARY FLOW CONTROL MEMBER

CROSS-REFERENCE TO RELATED APPLICATION

This application is a Section 371 of International Application No. PCT/IL2011/000829, filed Oct. 27, 2011, which was published in the English language on May 18, 2012, under International Publication No. WO 2012/063230 A1, and the disclosure of which is incorporated herein by reference.

FIELD OF THE INVENTION

The invention relates to inline liquid drug medical devices for liquid drug reconstitution and administration purposes.

BACKGROUND OF THE INVENTION

Commonly owned U.S. Pat. No. 6,238,372 entitled Fluid Control Device illustrates and describes a fluid control device for use with a syringe and at least one medicinal vessel. The fluid control device includes a first port, a second port for receiving the syringe, a third port including an adaptor having a fluid conduit member extending into the interior of the medicinal vessel when attached thereto and a flow control member selectively disposable from a first flow control position enabling a flow path between a first pair of two ports and second flow control position enabling a flow path between a second pair of two ports. The flow control member is coupled to one of the ports for manipulation between its flow control positions.

Commonly owned PCT International Application No. PCT/IL2005/000376 entitled Liquid Drug Medical Devices and Needle Shield Removal Device and published under PCT International Publication WO 2005/105014 illustrates and describes a liquid drug medical device for liquid drug reconstitution and administration purposes, a vial adapter with elastomer tubing and a needle shield removal device. The liquid drug medical device has a longitudinal device axis and is intended for use with a source of physiological solution and a medicinal vessel. The liquid drug medical device includes a body member having a first port for fluid connection with the source of physiological solution and a flow control member rotatably mounted in the body member about an axis of rotation co-axial with the device axis. The flow control member has a first major flow duct and a second major flow duct substantially parallel to and non-coaxial with the device axis and respectively terminating at a second port, and a third port for administering the liquid drug. The liquid drug medical device further includes a manually rotatable adapter having a fluid conduit member with a proximal end in flow communication with the second port and a distal end extending into the medicinal vessel on its attachment to the adapter, and coupled to the flow control member for rotating same between a first flow control position for connecting the first port with the second port, and a second flow control position for connecting the first port with the third port.

Commonly owned PCT International Application No. PCT/US2008/070024 entitled Medicament Mixing and Injection Apparatus and published under PCT International Publication No. WO 2009/038860 illustrates and describes a mixing and injection apparatus including a needle and a needle base, a syringe attachment element and a mixing chamber engagement assembly including a needle chamber surrounding the needle and a first liquid conduit portion, sealed from the needle chamber and a mixing chamber engagement portion including a second liquid conduit portion communicating with the first liquid conduit portion and configured for communication with a mixing chamber. The syringe attachment element and the needle base are configured to permit liquid communication between an interior of the syringe and the first liquid conduit portion when the syringe attachment element and the needle base are in the first relative engagement orientation and to permit liquid communication between an interior of the syringe and the needle when the syringe attachment element and the needle base are in the second relative engagement orientation, axially separated from the first relative orientation along the injection axis.

Commonly owned PCT International Application No. PCT/IL2010/000915 entitled Inline Liquid Drug Medical Devices with Linear Displaceable Sliding Flow Control Member and published under PCT International Publication No. WO 2011/058548 illustrates and describes inline liquid drug medical devices having a longitudinal device axis, a housing with a linear displaceable sliding flow control member displaceable along a transverse bore from a first flow control position for establishing flow communication between a first pair of ports for liquid drug reconstitution purposes to a second flow control position for establishing flow communication between a second pair of ports for liquid drug administration purposes, and a manually operated actuating mechanism for applying a linear displacement force for urging the flow control member to slide along the bore from its first flow control position to its second flow control position.

SUMMARY OF THE INVENTION

The present invention is directed toward inline liquid drug medical devices for use with a source of physiological fluid and a medicinal vessel for liquid drug reconstitution and administration purposes. The inline liquid drug medical devices include a housing having a longitudinal device axis and a vial adapter removably attached to the housing and detachable therefrom along a line of detachment co-directional with the device axis. The housing includes a port manifold having a first port for fluid connection with a source of physiological fluid and a drug dispensing port fitted with a drug dispenser such as a needle, an atomizer, and the like, for liquid drug administration purposes. The first port and the drug dispensing port are co-axial with the device axis for facilitating intuitive use of the device. The inline liquid drug medical device further includes a rotary flow control member rotatably mounted on the port manifold about an axis of rotation co-axial with the device axis. The flow control member includes a second port for flow communication with a medicinal vessel for liquid drug reconstitution purposes. The vial adapter is configured to be manually unthreaded from the housing for transposing the flow control member from an initial first flow control position for enabling flow communication between the first port and the second port for liquid drug reconstitution purposes to a subsequent second flow control position for enabling flow communication between the first port and the drug dispensing port for liquid drug administration purposes.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 4A is a longitudinal cross section of FIG. 1's device along line A-A in FIG. 1 showing the flow control member in an initial first flow control position for liquid drug reconstitution purposes and the vial adapter in an initial liquid drug reconstitution position;

FIG. 4B is an enlarged cross-section view of the housing in FIG. 4A;

DETAILED DESCRIPTION OF PREFERRED EMBODIMENTS OF THE INVENTION

Figure 1:
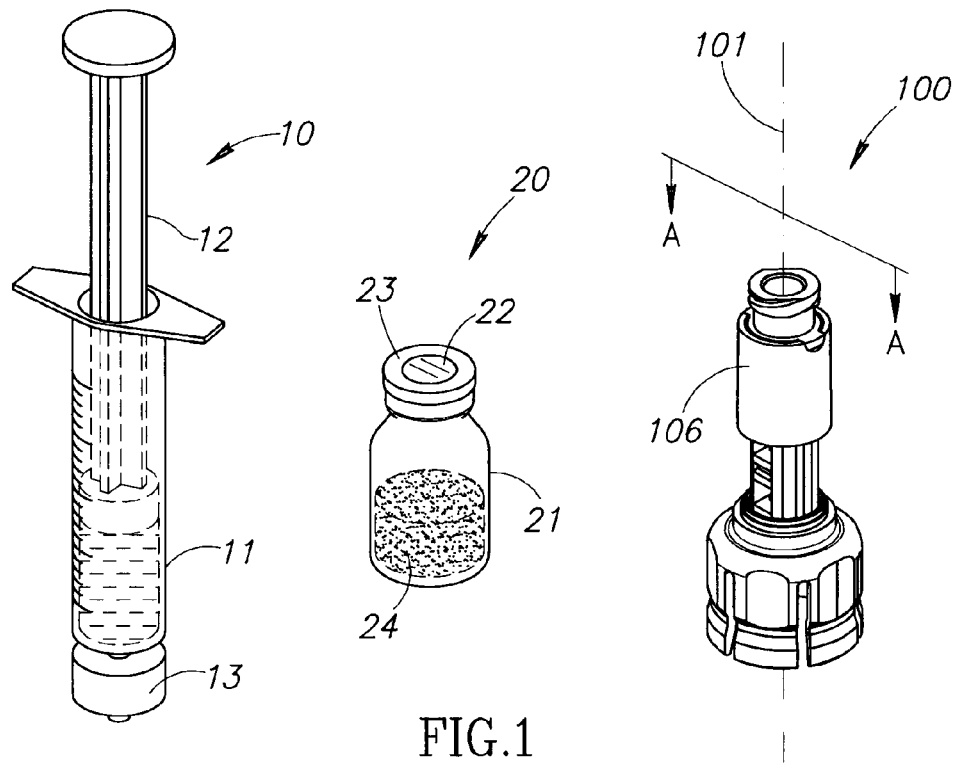
FIG. 1 is a pictorial representation of a syringe, a drug vial and an inline liquid drug medical device having a housing, a rotary flow control member and a manually rotatable vial adapter.
Figure 2:
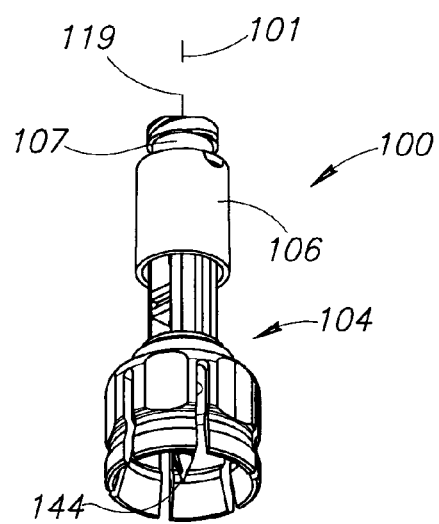
FIG. 2 is a perspective view of FIG. 1's device.
Figure 3:
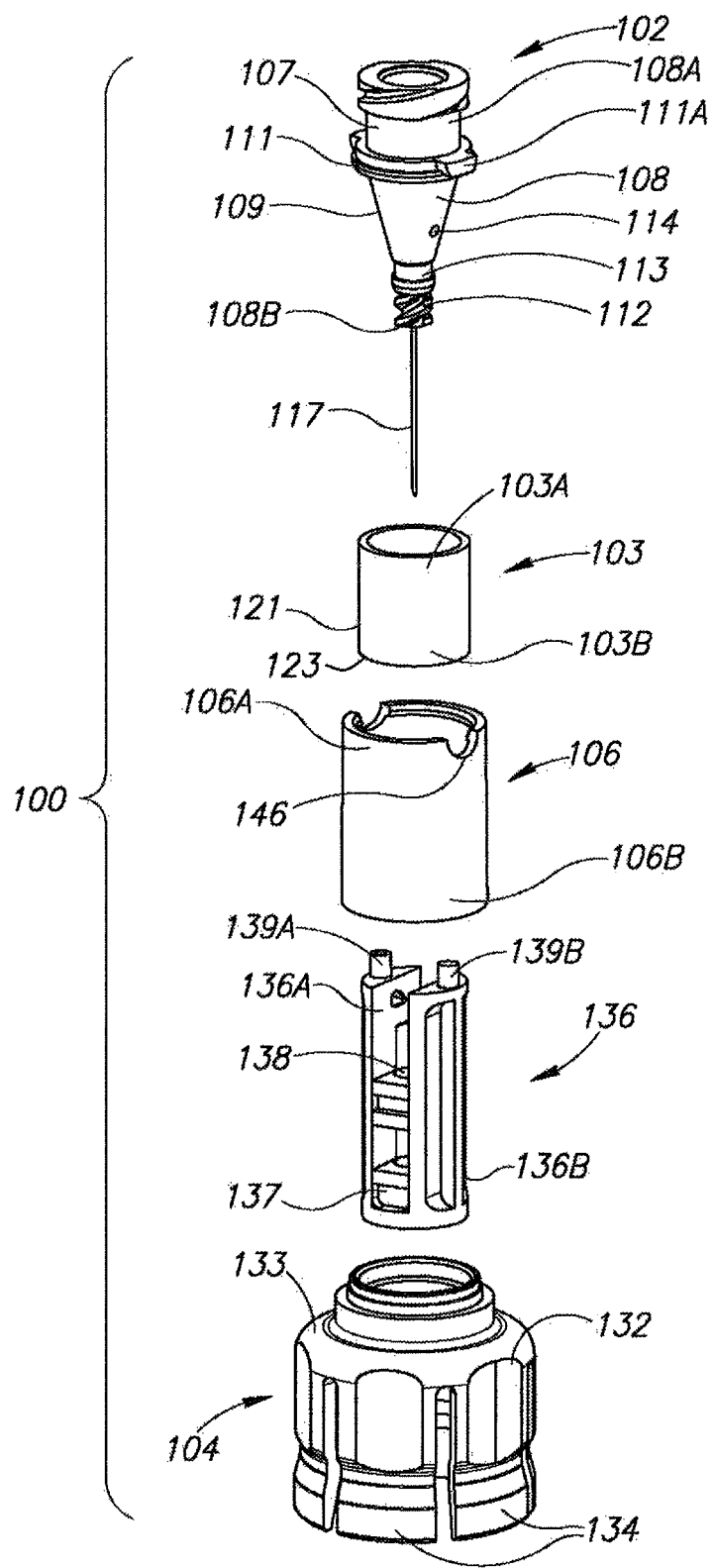
FIG. 3 is an exploded view of FIG. 1's device.
Figure 5B:
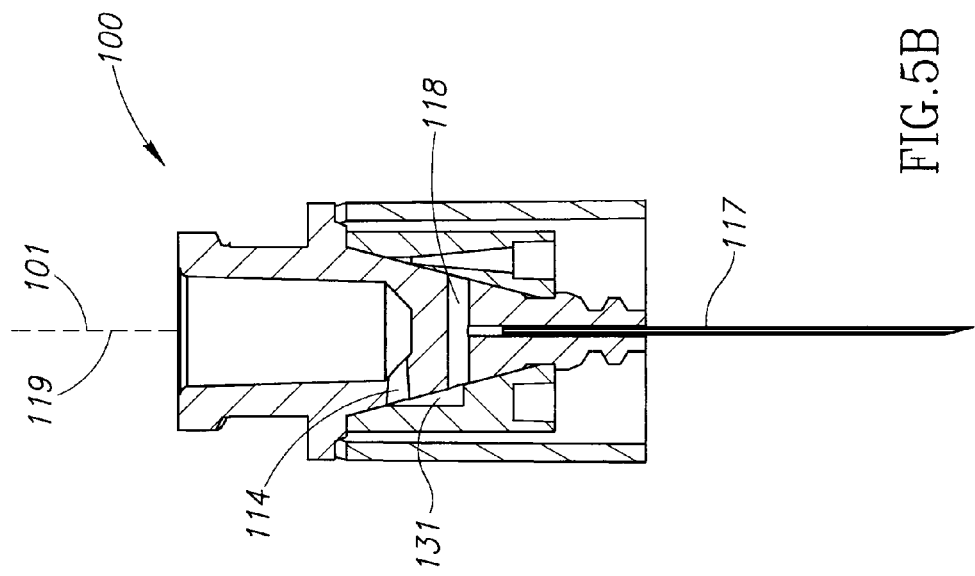
FIG. 5B is an enlarged cross section view of the device in FIG. 5A.
Figure 5A:
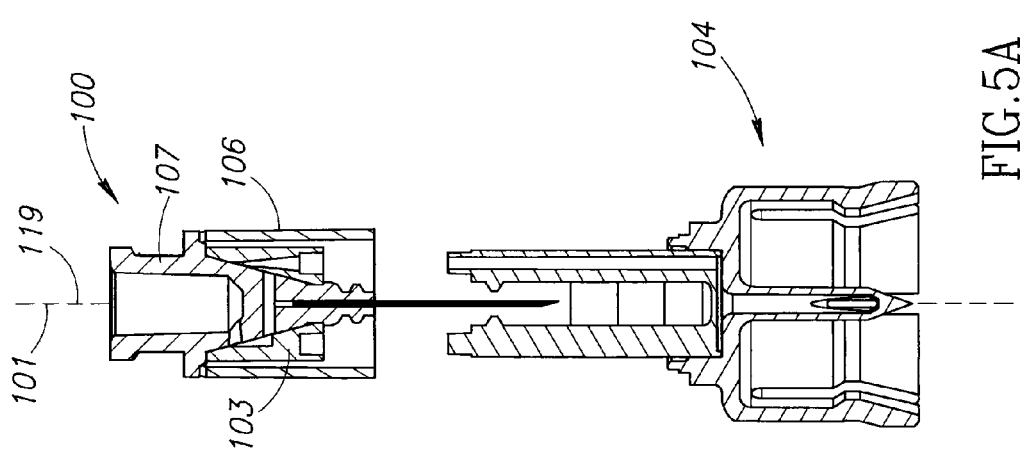
FIG. 5A is a longitudinal cross section of FIG. 1's device along line A-A in FIG. 1 showing its flow control member in a second flow control position for liquid drug administration purposes and its vial adapter detached from its housing.

FIG. 1 shows a syringe 10 constituting a source of physiological fluid, a drug vial 20 constituting a medicinal vessel and an inline liquid drug medical device 100 for use with the syringe 10 and the drug vial 20. The syringe 10 includes a barrel 11 with a plunger 12 and a male Luer lock connector 13. The syringe 10 can be formed with other types of connectors. The drug vial 20 includes an open topped bottle 21 sealed by a vial stopper 22 capped by a band 23 or other suitable capping material. The vial 20 contains either a powdered or liquid drug 24. The syringe 10 typically contains diluent for reconstituting the vial contents 24.

FIGS. 2 to 5B show the inline liquid drug medical device 100 having a longitudinal device axis 101 and including a housing 102, a rotary flow control member 103, a manually rotatable vial adapter 104, and a rigidly mounted tubular sleeve 106. The housing 102 includes a syringe port 107 constituting a first port co-axial with the device axis 101. The syringe port 107 is typically implemented as a female Luer connector for screw thread engagement with the male Luer lock connector 13. The housing 102 includes a conical shaped port manifold 108 integrally formed with the syringe port 107 and tapering from a wide diameter proximal port manifold end 108A adjacent the syringe port 107 towards a threaded distal port manifold end 108B.

The port manifold 108 includes a conical peripheral port manifold surface 109 and a rim 111 circumferentially surrounding the proximal port manifold end 108A having two opposing radial extending fastening wings 111A. The port manifold 108 includes a fastening thread 112 at its distal port manifold end 108B for screw thread engagement between the housing 102 and the vial adapter 104. The distal port manifold end 108B includes a port manifold shoulder 113 for securing the flow control member 103 thereon.

The port manifold 108 includes a minor flow duct 114 transverse to the device axis 101 and extending radial from the syringe port 107 to the peripheral port manifold surface 109. The port manifold 108 includes a drug dispensing port 116 constituting a third port coaxial with the device axis 101 and the syringe port 107. The drug dispensing port 116 extends midway between the syringe port 107 and the distal port manifold end 108B to the distal port manifold end 108B. The drug dispensing port 116 is preferably fitted with a drug dispensing device in the form of a needle 117, a spray nozzle, and the like, for liquid drug administration purposes. The port manifold 108 includes a throughgoing bore 118 transverse to the device axis 101 and in flow communication with the drug dispensing port 116 such that they resemble a T-shape.

The flow control member 103 is rotatably mounted on the port manifold 108 about an axis of rotation 119 co-axial with device axis 101, the syringe port 107 and the drug dispensing port 116. The flow control member 103 has a cylindrical outer wall 121 and a conical inner wall 122 facing the port manifold 108 for sealing mounting thereon. The flow control member 103 includes a proximal flow control member end 103A and a distal flow control member end 103B. The flow control member 103 is shorter than the port manifold 108 and is mounted thereon such that the distal port manifold end 108B protrudes through the distal flow control member end 103B. The distal flow control member end 103B has an underside surface 123 formed with a cavity 124 and an opposite blind cavity 126.

The flow control member 103 includes an axial directed liquid drug reconstitution channel 127 having a proximal opening 128 and terminating at a distal second port 129 constituted by the cavity 124. The proximal opening 128 is in flow communication with the minor flow duct 114 in an initial first flow control position of the flow control member 103 for establishing flow communication between the syringe port 107 and the second port 129 (see FIGS. 4A and 4B). The flow control member 103 includes an axial liquid drug administration channel 131 formed in its inner conical wall 122 in flow communication with the minor flow duct 114 when the flow control member 103 is in a subsequent second flow control position for establishing flow communication between the syringe port 107 and the drug dispensing port 116 (see FIGS. 5A and 5B).

The vial adapter 104 includes a skirt 132 with a top surface 133 and downward depending flex members 134 for snap fitting onto the drug vial 20. The vial adapter 104 includes an elongated upright stem 136 having two opposing parallel curved stem walls 136A and 136B lateral to the device axis 101. The stem 136 includes annular stem ribs 137 in a transverse direction to the device axis 101. The stem ribs 137 are formed with throughgoing apertures 138 for receiving the needle 117 on coupling the vial adapter 104 on the housing 102. The stem wall 136A terminates in a stem tip connector 139A and the stem wall 136B terminates in a stem tip connector 139B. Each stem wall 136 has an engagement tooth 141 for engaging the fastening thread 112 for detachably coupling the vial adapter 104 to the housing 102. The stem tip connectors 139A and 139B respectively fit into the cavities 124 and 126 for coupling the vial adapter 104 to the flow control member 103 in the initial liquid drug reconstitution position of the vial adapter 104 for enabling the vial adapter 104 to rotate the flow control member 103 therewith relative to the port manifold 108.

The stem wall 136A includes a fluid conduit 142 co-directional with the device axis 101 and lateral thereto. The fluid conduit 142 has a proximal fluid conduit end 142A in the stem tip connector 139A for sealing insertion in the second port 129. The fluid conduit 142 has a distal end 142B in flow communication with a radial fluid interconnect conduit 143. The fluid interconnect conduit 143 is in flow communication with a co-axial puncturing cannula 144 for puncturing the vial stopper 22 on snap fit mounting of the vial adapter 104 on the drug vial 20. The puncturing cannula 144 extends slightly therebeyond so that on inverting the drug vial 20 nearly the entire liquid drug contents can be aspirated therefrom through the puncturing cannula 144.

In the first flow control position, the fastening thread 112 is engaged by the engagement teeth 141 to prevent the vial adapter 104 being separated from the housing 102. As the vial adapter 104 is rotated to unthread the engagement teeth 141 from the fastening thread 112, the vial adapter 104 simultaneously rotates the flow control member 103 from its first flow control position to its second flow control position. The engagement teeth 141 fully disengage from the fastening thread 112 after transposing the flow control member 103 to its second flow control position, at which time the vial adapter 104 is fully detachable from the housing 102 along a line of separation co-directional with the device axis 101.

The sleeve 106 includes a proximal sleeve end 106A with a pair of fastening slots 146 for fastening onto the fastening wings 111A for securing the sleeve 106 onto the housing 102 and a distal sleeve end 106B terminating at the distal port manifold end 108B. The sleeve 106 surrounds the flow control member 103 for enabling convenient user holding of the inline liquid drug medical device 100.

Figure 6D:
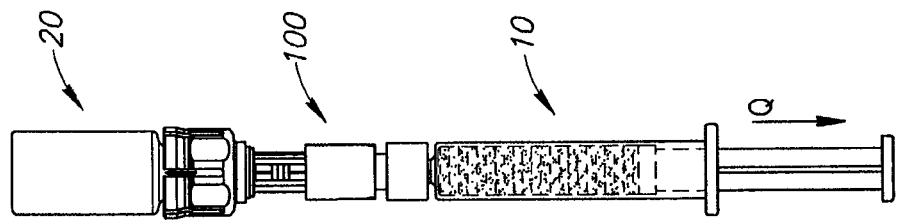
FIGS. 6A to 6G show the use of FIG. 1's device for liquid drug reconstitution and administration purposes.
Figure 6C:
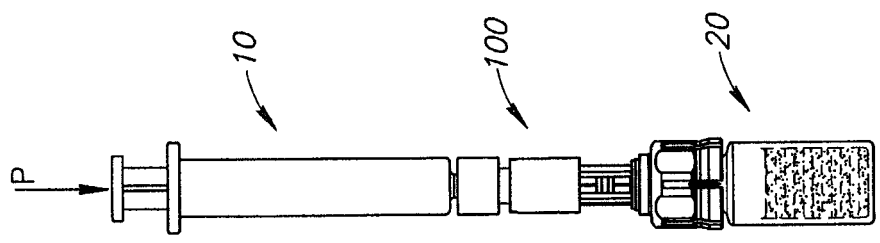
Figure 6B:
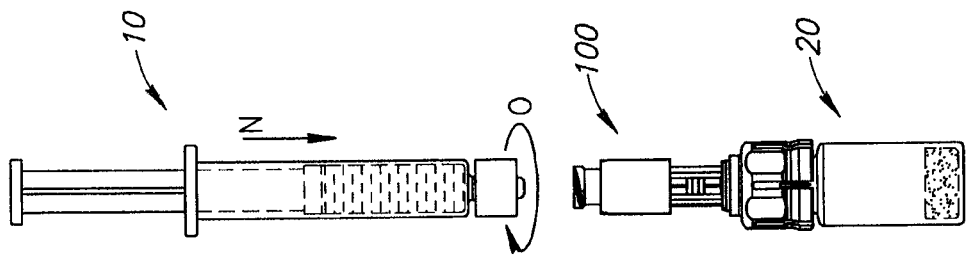
Figure 6A:
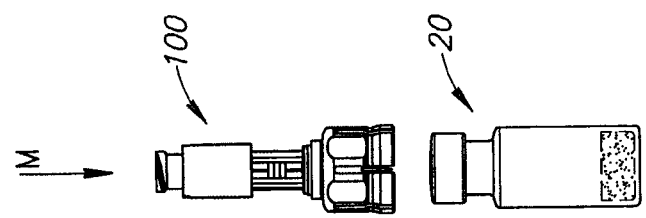

FIGS. 6A to 6G show the use of the inline liquid drug medical device 100 for liquid drug reconstitution and administration purposes as follows:

FIG. 6A shows the device 100 in its initial state ready for liquid drug reconstitution. The vial adapter is threaded on the housing in its initial liquid drug reconstitution position and engages the flow control member in its initial first flow control position for stabling flow communication between the syringe port and puncturing cannula. A user holds the sleeve and mounts the device 100 on a drug vial 20, as indicated by arrow M.

FIG. 6B shows the user approximating the syringe 10 towards the device 100, as indicated by arrow N, and screw threading the syringe 10 onto the device 100, as indicated by arrow O.

FIG. 6C shows the user injecting the syringe's contents into the drug vial 20, as indicated by arrow P. The user agitates the assemblage for reconstituting the liquid drug.

FIG. 6D shows the user inverting the assemblage and aspirating the reconstituted liquid drug contents into the syringe 10, as indicated by arrow Q.

Figures 6E, 6F, 6G:
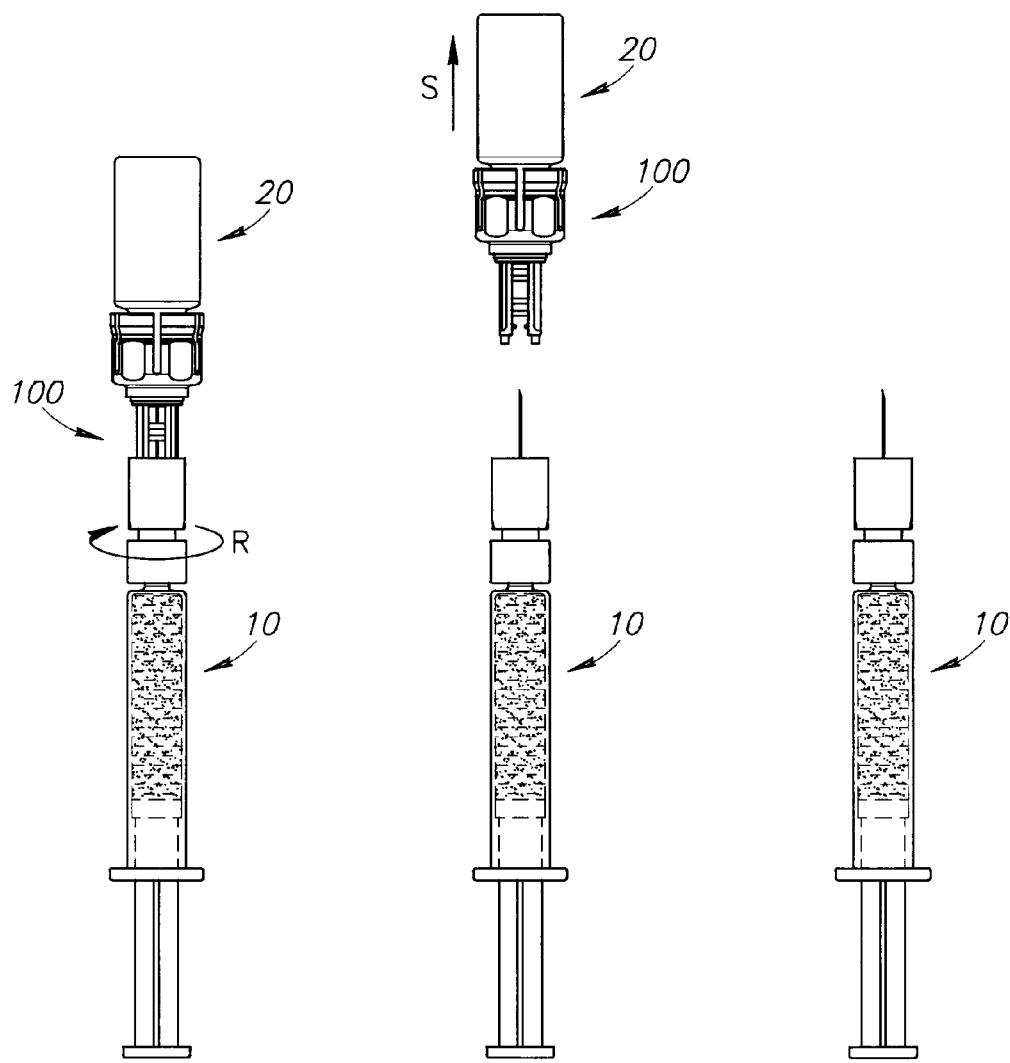

FIG. 6E shows the user rotating the vial adapter relative to the housing as indicated by arrow S for simultaneously transposing the flow control member to its subsequent second flow control position and detaching the vial adapter from the housing as indicated by arrow S (see FIG. 6F). In this position, the syringe port is in flow communication with the drug dispensing port and the needle is exposed for administration purposes (see FIG. 6G).

While the invention has been described with respect to a limited number of embodiments, it will be appreciated that many variations, modifications, and other applications of the invention can be made within the scope of the appended claims. For example, the stem can include a solid piece formed with a fluid conduit and a blind needle bore.

The invention claimed is:

1. An inline liquid drug medical device for use with a source of physiological solution and a medicinal vessel for reconstitution and administration of a liquid drug, the inline liquid drug medical device having a longitudinal device axis, and comprising:

a) a housing including a first port for fluid connection with the source of physiological solution, and an integrally formed port manifold having a peripheral port manifold surface and a drug dispensing port for liquid drug administration, said first port and said drug dispensing port being co-axial with the device axis, said port manifold including a minor flow duct transverse to the device axis extending radially from said first port to said peripheral port manifold surface, and a bore transverse to the device axis and in flow communication with said drug dispensing port;

b) a rotary flow control member having a second port, an inner wall facing said port manifold and an axial liquid drug administration channel, said rotary flow control member being rotatable on said port manifold about an axis of rotation co-axial with the device axis, said first port and said drug dispensing port from an initial first flow control position for establishing flow communication between said first port and said second port for liquid drug reconstitution purposes to a subsequent second flow control position for establishing flow communication between said first port and said drug dispensing port via said axial liquid drug administration channel and said bore for liquid drug administration purposes; and c) a manually rotatable vial adapter for snap fitting onto the medicinal vessel and including an elongated upright stem for initial engagement with said flow control member in said initial first flow control position in an initial liquid drug reconstitution position of said vial adapter, said vial adapter having a fluid conduit co-directional the device axis and lateral thereto, said fluid conduit having a proximal end in flow communication with said second port and a distal end in flow communication with a puncturing cannula extending into the medicinal vessel on attachment to said vial adapter in said initial liquid drug reconstitution position, said vial adapter being manually rotationally detachable from said housing along a line of detachment co-directional with the device axis for simultaneously transposing said flow control member from said initial first flow control position to said subsequent second flow control position.

2. The device according to claim 1, wherein said elongated upright stem includes two opposing spaced apart stem walls separated by at least one transverse stem rib wherein one stem wall includes said fluid conduit and an arrangement for receiving a needle disposed in said drug dispensing port.

3. The device according to claim 2, wherein said housing further includes a fixedly mounted sleeve encircling said flow control member for assisting a user to operate the device by enabling the user to grip said sleeve in one hand and rotate said vial adapter relative to said housing with another hand.

4. The device according to claim 1, wherein said housing further includes a fixedly mounted sleeve encircling said flow control member for assisting a user to operate the device by enabling the user to grip said sleeve in one hand and rotate said vial adapter relative to said housing with another hand.

* * * * *